(12) United States Patent
Tallent et al.

(10) Patent No.: US 12,165,767 B2
(45) Date of Patent: Dec. 10, 2024

(54) SYSTEM AND METHOD FOR IDENTIFICATION OF REMOTELY ACCESSED PATIENT DEVICE

(71) Applicant: Hill-Rom Services, Inc., Batesville, IN (US)

(72) Inventors: Dan R. Tallent, Hope, IN (US); Eric D. Benz, Sunman, IN (US); Aziz Ali Bhai, Fishers, IN (US); Unnati Ojha, Apex, NC (US); Nicholas Comparone, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 621 days.

(21) Appl. No.: 17/395,515

(22) Filed: Aug. 6, 2021

(65) Prior Publication Data
US 2022/0044799 A1    Feb. 10, 2022

Related U.S. Application Data

(60) Provisional application No. 63/063,632, filed on Aug. 10, 2020.

(51) Int. Cl.
*G16H 40/63*    (2018.01)
*G05B 19/042*    (2006.01)

(52) U.S. Cl.
CPC ........... *G16H 40/63* (2018.01); *G05B 19/042* (2013.01); *G05B 2219/2608* (2013.01)

(58) Field of Classification Search
CPC .................. G16H 40/63; G05B 19/042; G05B 2219/2608
See application file for complete search history.

(56) References Cited

U.S. PATENT DOCUMENTS

| | | | |
|---|---|---|---|
| 6,727,818 B1 * | 4/2004 | Wildman | G16H 40/20 340/567 |
| 6,762,681 B1 * | 7/2004 | Danelski | G06Q 10/087 340/568.1 |
| 7,538,670 B2 * | 5/2009 | Smith | G08B 13/1436 340/572.1 |
| 8,572,778 B2 | 11/2013 | Newkirk et al. | |
| 9,492,341 B2 | 11/2016 | Huster et al. | |
| 9,655,798 B2 * | 5/2017 | Zerhusen | A61G 7/015 |
| 10,290,071 B2 * | 5/2019 | Heil | G16H 20/30 |
| 10,373,226 B1 * | 8/2019 | Russell | G06Q 30/0635 |

(Continued)

*Primary Examiner* — Steven Lim
*Assistant Examiner* — Son M Tang
(74) *Attorney, Agent, or Firm* — Price Heneveld LLP

(57) ABSTRACT

A patient support apparatus includes a visual indicator in connection with a portion of the patient support apparatus. The visual indicator is configured to output a first indication and a second indication. The support apparatus also includes a communication circuit configured to communicate via a wireless communication interface and a controller configured to communicate with a service unit via the wireless communication interface. The controller is configured to activate the first indication in response to the service unit detected within a detection range, and in response to enabling a remote access to the service unit, the controller is configured to activate the second indicator. The activation of the second indicator identifies the controller of the patient support apparatus in communication with the service unit via the wireless communication interface.

22 Claims, 8 Drawing Sheets

(56) References Cited

U.S. PATENT DOCUMENTS

| | | | | |
|---|---|---|---|---|
| 2002/0014951 | A1* | 2/2002 | Kramer | G16H 10/60 340/286.07 |
| 2004/0148491 | A1* | 7/2004 | Damron | G06F 9/3851 712/E9.05 |
| 2006/0290519 | A1* | 12/2006 | Boate | G07C 9/28 340/573.4 |
| 2014/0297327 | A1* | 10/2014 | Heil | G16H 40/40 700/282 |
| 2015/0082295 | A1* | 3/2015 | Collins, Jr. | G07C 3/00 717/170 |
| 2015/0178529 | A1* | 6/2015 | Theurer | G16H 40/67 340/10.1 |
| 2016/0005300 | A1* | 1/2016 | Laufer | H04W 4/33 340/8.1 |
| 2017/0124844 | A1* | 5/2017 | Huster | A61G 7/012 |
| 2018/0161225 | A1* | 6/2018 | Zerhusen | A61G 7/05 |
| 2018/0184984 | A1* | 7/2018 | Zerhusen | A61B 5/7282 |
| 2019/0020971 | A1* | 1/2019 | Ginsberg | H04W 4/023 |
| 2019/0152376 | A1* | 5/2019 | Schwartz | G06Q 10/08 |

* cited by examiner

SYSTEM AND METHOD FOR IDENTIFICATION OF REMOTELY ACCESSED PATIENT DEVICE

CROSS-REFERENCE TO RELATED APPLICATIONS

This application claims priority under 35 U.S.C. § 119(e) and the benefit of U.S. Provisional Application No. 63/063,632 entitled SYSTEM AND METHOD FOR IDENTIFICATION OF REMOTELY ACCESSED PATIENT DEVICE, filed on Aug. 10, 2020, by Dan R. Tallent, et al., the entire disclosure of which is incorporated herein by reference.

FIELD OF THE DISCLOSURE

The present disclosure generally relates to a system and method for identifying a device in wireless connection with a control apparatus and more specifically relates to a patient support apparatus comprising a connection indicator configured to identify a connection status with a service unit.

SUMMARY OF THE DISCLOSURE

According to one aspect of the present disclosure, a patient support apparatus including a connection indicator is disclosed. The apparatus comprises a visual indicator in connection with a portion of the patient support apparatus. The visual indicator is configured to output a first indication and a second indication. The support apparatus comprises a communication circuit configured to communicate via a wireless communication interface and a controller configured to communicate with a service unit via the wireless communication interface. The controller is configured to activate the first indication in response to the service unit detected within a detection range, and, in response to enabling a remote access to the service unit, the controller is configured to activate the second indicator. The activation of the second indicator identifies the controller of the patient support apparatus is in communication with the service unit via the wireless communication interface.

According to another aspect of the disclosure, a method for operating a patient support apparatus is disclosed. The method comprises monitoring a wireless communication interface for a service unit and detecting the service unit within a detection range. In response to detecting the service unit within the detection, a first indication of a visual indicator is activated. The method further comprises receiving an authentication from the remote service unit and enabling a remote access to a controller of the patient support apparatus in response to the authentication. In response to enabling the remote access to the controller, a second indication of the visual indicator is activated. The second indication identifies the controller in communication with the service unit via the wireless communication interface.

According to yet another aspect of the disclosure, a patient support apparatus includes a visual indicator in connection with a portion of the patient support apparatus. The visual indicator is configured to output a first indication and a second indication from the portion of the patient support apparatus. A communication circuit is configured to communicate via a wireless communication interface. A controller is configured to communicate with a service unit via the wireless communication interface. In operation, the controller activates the first indication in response to the service unit detected within a detection range of the wireless communication interface. The controller may further receive a control instruction from the service unit via the wireless communication interface. In response to processing the control instruction, the controller activates the second indicator identifying a confirmation of a completion of the control instruction.

These and other features, advantages, and objects of the present invention will be further understood and appreciated by those skilled in the art by reference to the following specification, claims, and appended drawings.

DETAILED DESCRIPTION

Figure 1:
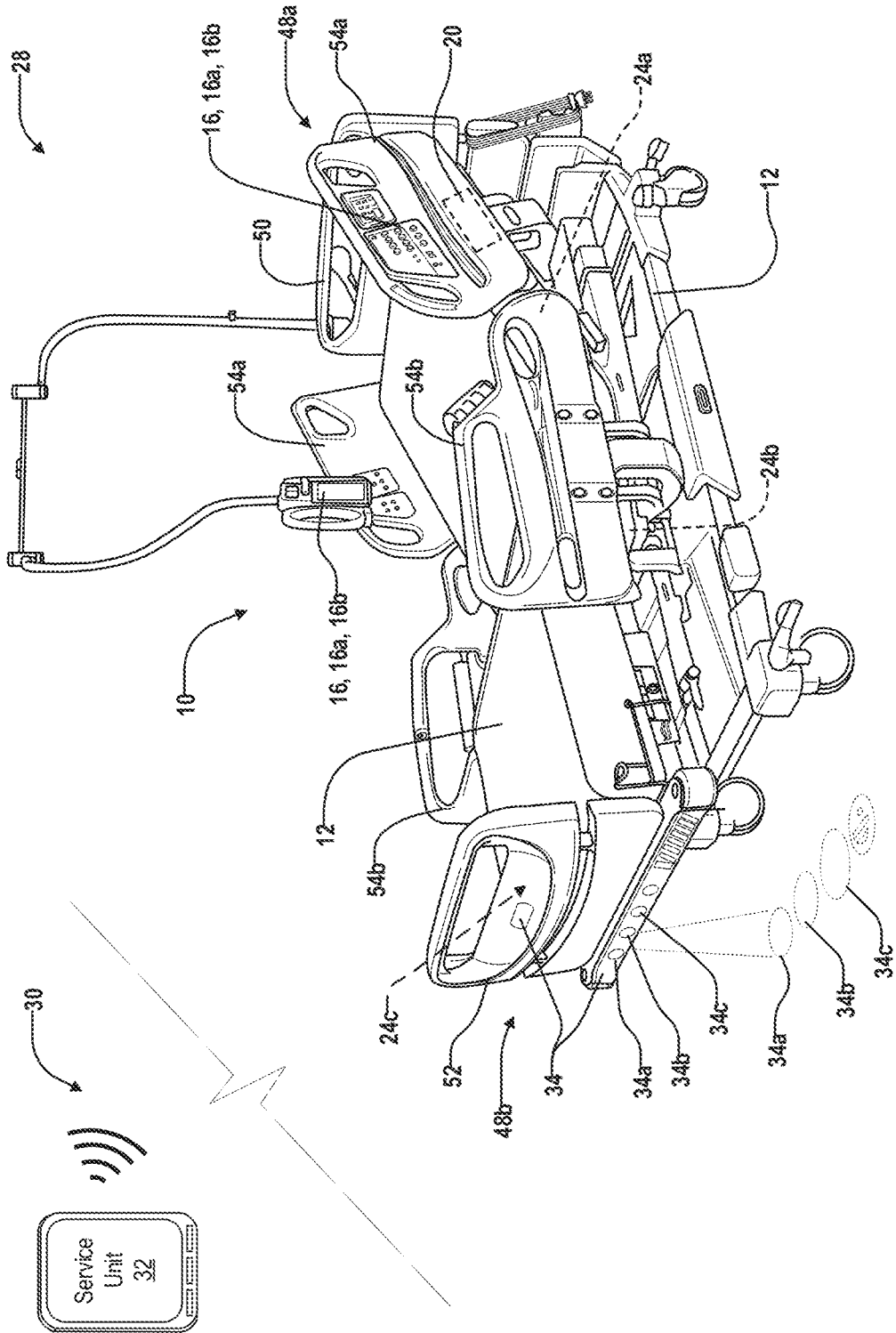
FIG. 1 is a perspective view of a patient support apparatus.

The presently illustrated embodiments reside primarily in combinations of method steps and apparatus components related to a method and system for completing a service operation for a patient support apparatus via a remote access procedure. Accordingly, various exemplary diagrams are presented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof shall relate to the disclosure as oriented in FIG. 1. Unless stated otherwise, the term "front" shall refer to a surface of the device closest to an intended viewer, and the term "rear" shall refer to a surface of the device furthest from the intended viewer. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Figure 2:
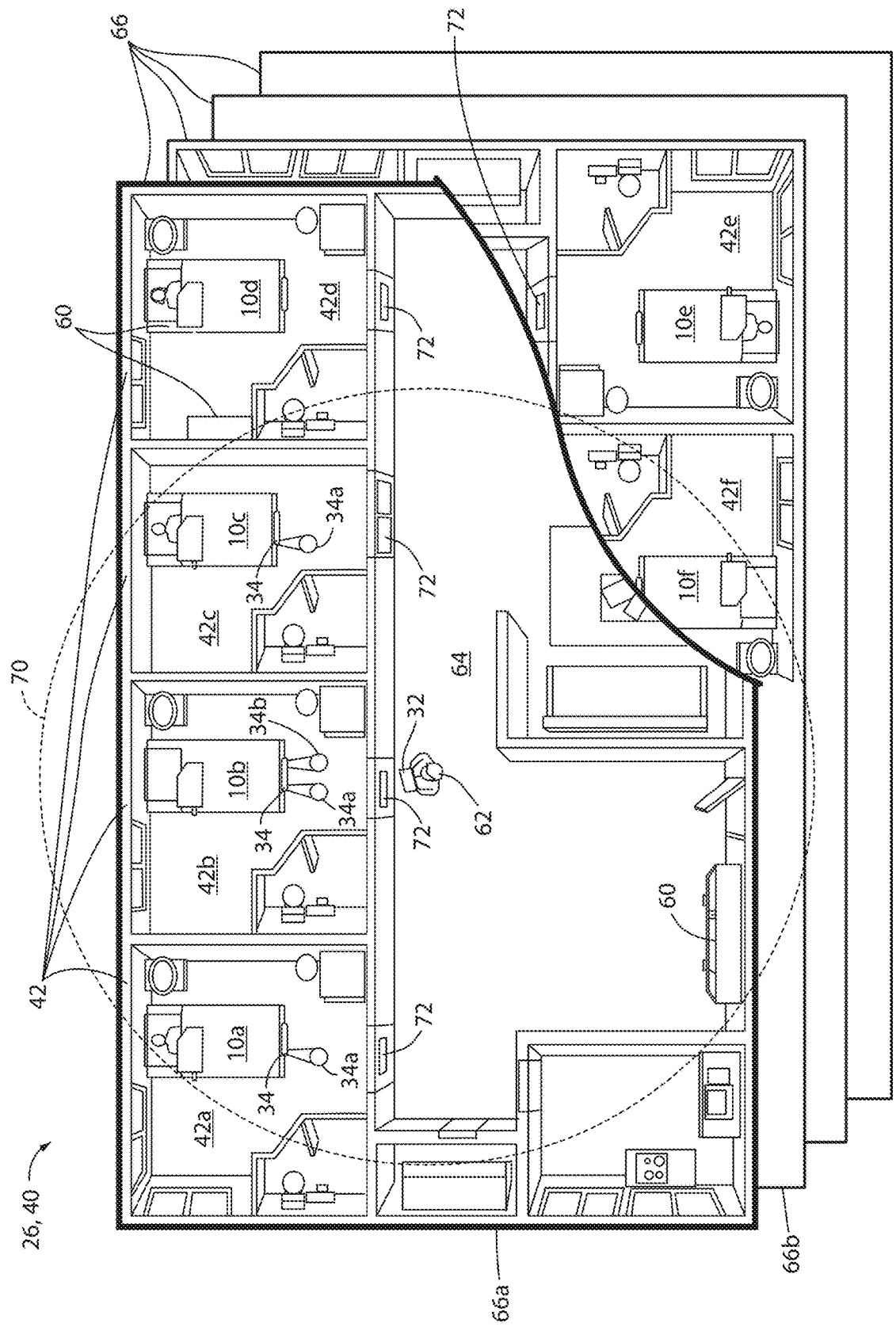
FIG. 2 is a perspective view of a hospital building demonstrating a plurality of patient suites including patient support apparatuses.
Figure 8:
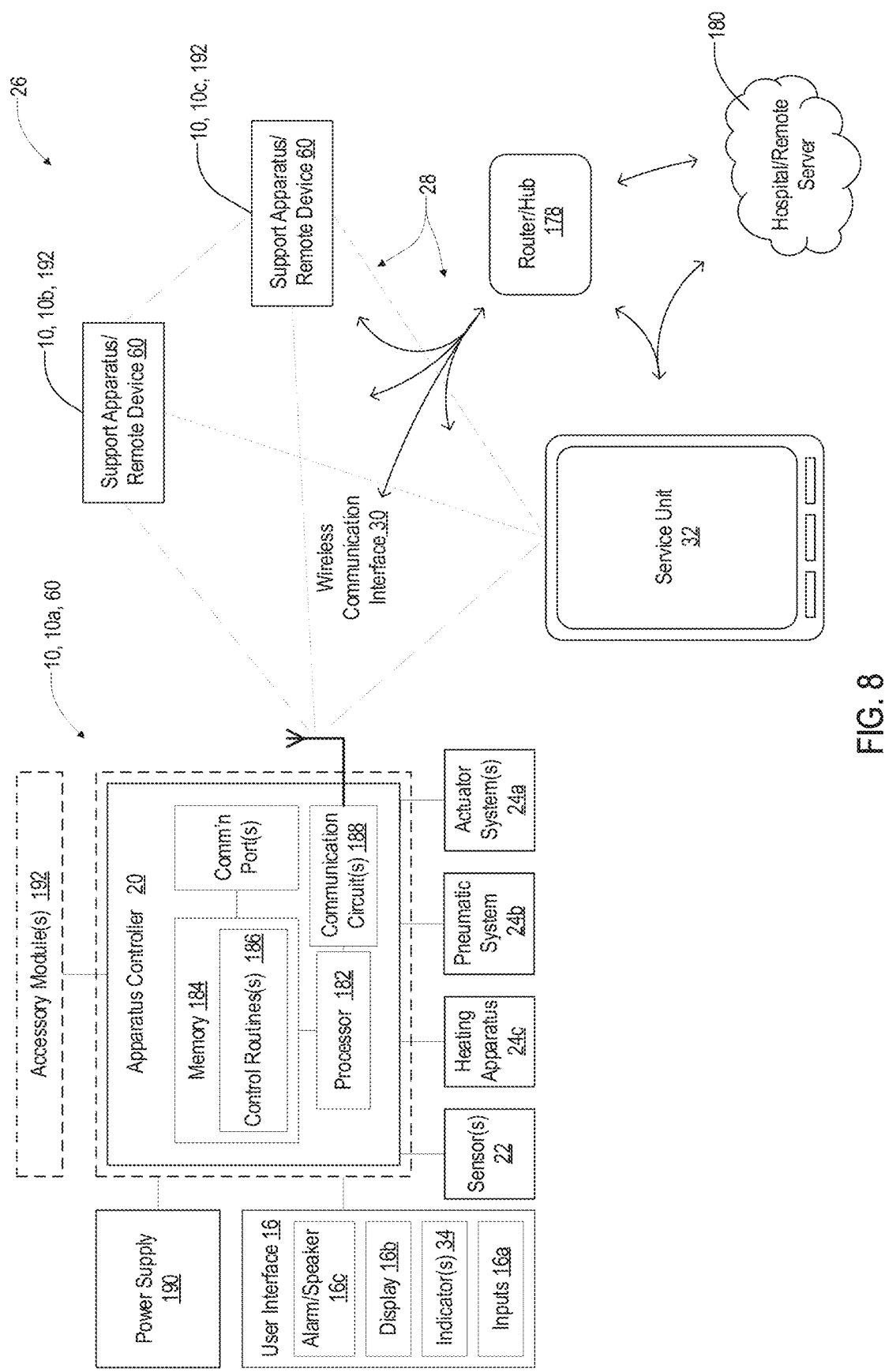
FIG. 8 is a block diagram of a service unit in wireless communication with a remotely accessed device in the form of a patient apparatus in accordance with the disclosure.

Referring to FIGS. 1, 2, and 8, reference numeral 10 generally designates a patient support apparatus in the form of a bed including a mattress 14 supported on a frame 12, a user interface 16, and a controller 20 configured to control functions of the support apparatus 10. In the exemplary implementations, the user interface 16 includes a plurality user inputs 16a and a status display 16b, which may correspond to a display screen or touch screen interface. In operation, the user interface 16 is configured to communicate with a controller 20. In this configuration, the user interface 16 provides status indications and feedback to a user of the support apparatus 10 in response to the user inputs 16a received by the user interface 16. The controller 20 is configured to control various features of the support apparatus 10 in response to inputs received via the user interface 16 as well as inputs received from various connected sensors 22 and service units or remote control devices as further discussed herein.

The operation of the patient support apparatus 10 may be the result of several integrated systems operating in coordination under the direction of the controller 20 as well as additional device-specific controllers. For example, the support apparatus 10 may include various control devices 24, such as an actuator system 24a, a pneumatic system 24b, and a heating apparatus 24c. Each of the control devices 24 may be controlled by the controller 20 to operate in response to the sensors 22 as well as the user inputs 16a and various automated or remotely controlled operations. Accordingly, the controller 20 of the support apparatus 10 may form a portion of a connected control system 26, which may be in communication with a hospital network 28 including one or more remote servers. The interconnected operation of the support apparatus provides for the associated features to operate via simple controls and further provides for integration with the hospital network 28. Additional details of the connected control system 26, including the control devices 24 and the sensors 22, are discussed in further detail in reference to FIG. 8.

The complex nature of the support apparatus 10 may introduce requirements for periodic maintenance and service updates that require on-site access by trained personnel. To facilitate such updates, the controller 20 of the support apparatus 10 includes a wireless communication interface 30 configured to wirelessly connect with a service unit 32. The connection between the controller 20 and the service unit 32 may provide for wireless, remote access to transmit service packages, software updates, driver updates, or similar configuration updates to the controller 20. However, as depicted in FIG. 2, a hospital building 40 or care facility may house a plurality of the support apparatuses 10 located in a plurality of patient suites or rooms 42. Additionally, each of the support apparatuses 10 may be portable, such that they are frequently be moved from one suite 42a to another suite 42b. Accordingly, the disclosure provides for an indicator device 34 or visual indicator comprising a plurality of indicators 34a, 34b, 34c on each of a plurality of support apparatuses 10a, 10b, 10c, etc. as demonstrated in FIG. 2. As discussed herein, the controller 20 is configured to control the indicator device 34 to: 1) identify when the service unit 32 is within a detection range; and 2) identify when the service unit 32 is connected to a specific support apparatus (e.g., a second apparatus 10b). In this way, the control system 26 may provide for secure operation between the service unit 32 and each of the controllers 20 of the support apparatuses 10.

As discussed herein, the service unit 32 may be implemented as a variety of electronic devices which may be in communication with one or more controllers 20 of the support apparatuses 10 via various communication protocols and corresponding communication circuits. For example, the service unit 32 may be embodied as a mobile device, smartphone, tablet, personal data assistant (PDA), laptop, computer, or various computerized devices and associated peripherals. The service unit 32 includes a communication circuit configured to communicate via a wireless communication protocol compatible with the communication circuit of the controller 20. The communication protocols may include one or more wireless protocols including, but not limited to, Bluetooth®; Bluetooth® Low Energy (BLE) Wi-Fi (802.11a, b, g, n, etc.); Ultra-Wideband (UWB); ZigBee®; and Z-Wave®; etc.). Accordingly, the control system 26 may be flexibly implemented to suit a variety of applications. Additional details of the connected control system 26, including the communication circuit of the controller 20, are shown and discussed in detail in reference to FIG. 8.

Referring now to FIG. 1, the patient support apparatus 10 may correspond to a hospital bed including the mattress 14 supported by the frame 12. While described as a hospital bed, it is within the scope of the disclosure that the patient support apparatus 10 may include a bed frame, a mattress, or any suitable structure for supporting a patient, including, but not limited to: other types of beds, surgical tables, examination tables, stretchers, and the like. As depicted, the support apparatus 10 includes a head end 48a and a foot end 48b. The bed or support apparatus 10 may further include a headboard 50 located proximate to the head end 48a and a footboard 52 located proximate to the foot end 48b. The support apparatus 10 further includes a pair of head side rail assemblies 54a and a pair of foot side rail assemblies 54b. In this configuration, the support apparatus 10 provides a secure apparatus for patient rest and recovery.

In some examples, the user interface 16 is coupled to an external side of one of the side rail assemblies 54a, 54b. The user interface 16 may be configured to accept a user input to communicate various control instructions to the controller 20 as well as provide a feedback indication of the operation of the support apparatus 10 to a user. While FIG. 1 illustrates the graphical user interface 16 coupled to the external side of at least one of the side rail assemblies 54a, 54b, it is also contemplated that the graphical user interface 16 may be coupled to any suitable component of the bed 10 for access by a user or caregiver. In some examples, the graphical user interface 16 may be coupled to the footboard 52 or the headboard 50.

The structure of the support apparatus 10 demonstrates an exemplary configuration of the included components and systems. Additional representative examples of user interfaces configured to receive user inputs can be found in U.S. Pat. Nos. 8,572,778 and 9,492,341, each of which is hereby incorporated by reference herein. Additionally, the user interface 16 may include a graphical user interface configured to communicate status and operating information, which may be detected by the sensors 22 (e.g., bed data, head of bed angle, patient weight). Exemplary details of the use of such user interfaces configured to control the support apparatus 10, patient beds, and devices other than patient beds may be found in U.S. Pat. No. 10,290,071, which is hereby incorporated by reference herein.

Referring now to FIGS. 1 and 2, the exemplary operation of the service unit 32 in an environment including a plurality of support apparatuses 10 is discussed. The exemplary operation is staged in the exemplary environment of the hospital building 40 including the patient suites 42. More generally, the patient support apparatuses 10 may be described as remotely accessed devices and referred to herein as remote devices 60 for clarity. Though specific methods and components of the system 26 are described in reference to the support apparatuses 10, the operation of the service unit 32 may generally apply to the remote devices 60. As discussed herein, the remote devices 60 represent various forms of devices operable to communicate via the wireless communication interface 30. Accordingly, it shall be understood that the specific example of the support apparatuses 10 as discussed herein shall not be considered limiting to the operation of the service unit 32.

In operation, a user 62 or service technician may transport the service unit 32 along hallways 64, which may be located on a plurality of floors 66 of the building 40. As depicted, a first floor 66a includes a first suite 42a, a second suite 42b, a third suite 42c, and a fourth suite 42d. Each of the suites 42 includes a corresponding support apparatus 10 or, more generally, a remote device 60 configured to communicate with the service unit 32. Accordingly, the suites 42 on the first floor 66a include a first support apparatus 10a, a second support apparatus 10b, a third support apparatus 10c, and a fourth support apparatus 10d. Additionally, a second-floor 66b of the building includes a fifth suite 42e and a sixth suite 42f that include a fifth support apparatus 10e and a sixth support apparatus 10f, respectively. Accordingly, without further identification available to the user 62, it may be challenging to distinguish the remote devices 60 (e.g., the patient support apparatuses 10) such that a specific device (e.g., the second support apparatus 10b) can be verified for maintenance or service.

Once activated in a service mode, the service unit 32 may be configured to detect a wireless broadcast signal from each of the remote devices 60 within a detection range 70 via the wireless communication interface 30. As depicted, each of the first support apparatus 10a, the second support apparatus 10b, the third support apparatus 10c, and the sixth support apparatus 10f are within the detection range 70 of the service unit 32. Accordingly, an application operating on the service unit 32 may present each of the remote devices 60 within the detection range 70. Additionally, once each of the support apparatuses 10a, 10b, 10c, and 10f is within the detection range 70, the corresponding controllers 20 may detect that the service unit 32 is nearby based on a wireless signal transmitted over the wireless communication interface 30. In response to identifying the wireless broadcast signal from the service unit 32, each of the controllers 20 of the support apparatuses 10 located within the detection range 70 may control the indicator device 34 or visual indicator to activate a first indicator 34a. In this way, the user 62 may be able to visually identify each of the patient support apparatuses 10 within the detection range 70 by simply viewing the first indicator 34a through a window 72.

The indicator device 34 may be embodied by a variety of devices, displays, emitters, light arrays, etc. For example, the indicator device 34 may correspond to a display screen (e.g. a liquid crystal display [LCD]) configured to illuminate in a first color or symbol to provide the first indicator 34a and a second color or symbol to provide for the second indicator 34b. Additionally, the indicator device 34 may include a third indicator 34c that may be illuminated as a third color or symbol on the display screen. Accordingly, a contiguous display screen or multi-color emitter may provide for the functionality of the first indicator 34a and the second indicator 34b. As shown in FIG. 1, the indicator device 34 comprises a plurality of emitters (e.g. light-emitting diodes [LEDs]) forming the first indicator 34a, the second indicator 34b, and/or the third indicator 34c located on a portion of the frame 12 proximate to the foot end 48b of the support apparatus 10.

In some examples, the indicator device 34 may include a projection device configured to project light from each of the indicators 34a, 34b, 34c onto a floor or wall located near the support apparatus 10 in the patient suite 42. The projection device may include an articulating emitter or projector configured to adjust a direction of the light output from the indicators 34a, 34b, 34c. In operation, light from the projection device may pass from the indicators 34a, 34b, 34c through cutouts and project images communicating the status of the support apparatus 10 identifying a proximity within the detection range 70 via the first indicator 34a and a connection status with the service unit 32 via the second indicator 34b. Additional examples of lights and indicators that may be used for the indicator device 34 or visual indicator are discussed in detail in U.S. Pat. No. 9,655,798 titled, "MULTI-ALERT LIGHTS FOR HOSPITAL BED," the disclosure of which is incorporated herein by reference. Though described as the first indicator 34a, the second indicator 34b, and the third indicator 34c in reference to specific functions or operational identifications, the indicator device 34 may be configured to output one or more indications to suit a variety of operations. Accordingly, the specific references to the first indicator 34a, the second indicator 34b, and the third indicator 34c are for clarity and the number of indicators and associated functions may vary without departing from the spirit of the invention.

Figure 3:
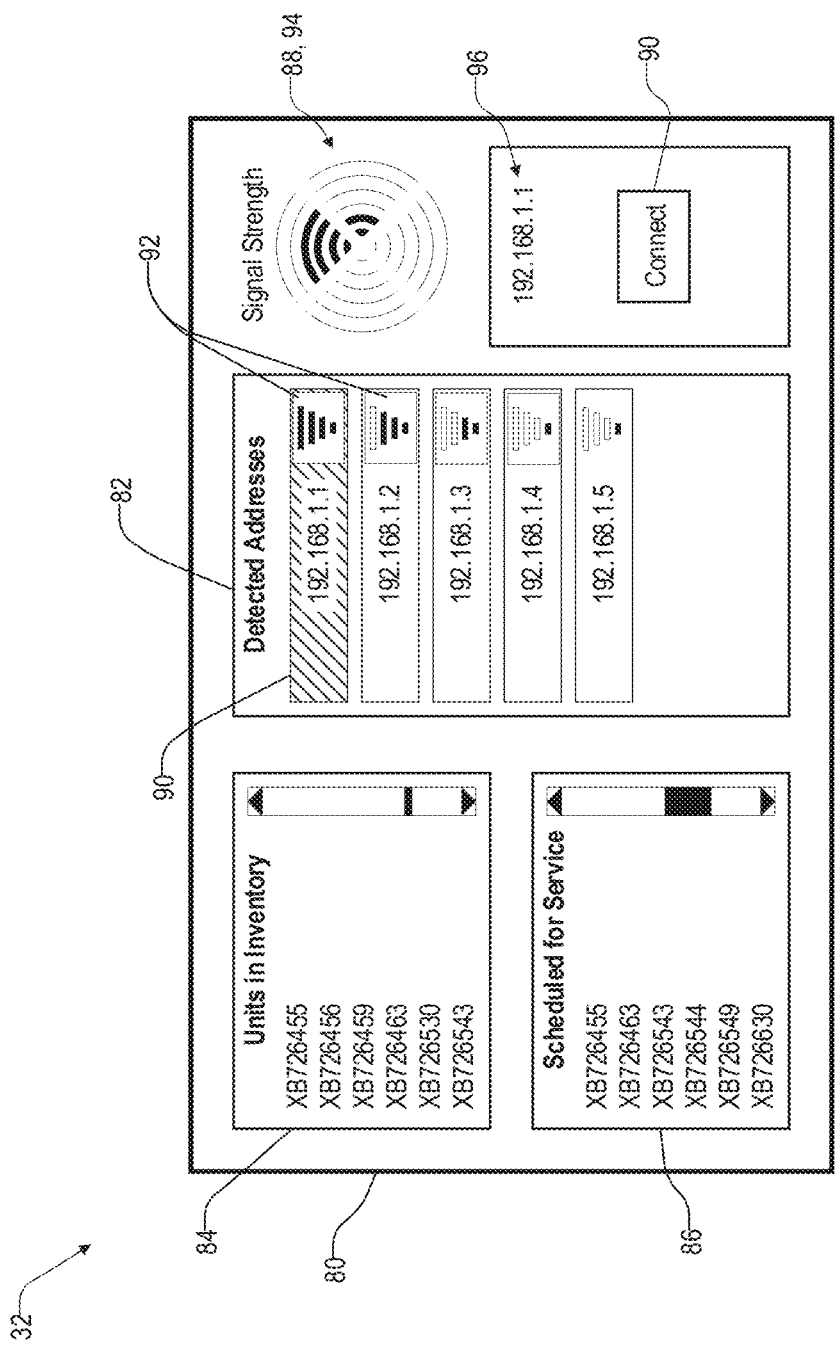
FIG. 3 is a graphical representation of an application interface of a service unit configured to remotely access a controller of the patient support apparatus.

As further discussed in reference to FIG. 3, the application or software operating on the service unit 32 may provide a list of addresses identifying the support apparatuses 10 within the detection range 70 of the wireless communication interface 30. However, the addresses of the support apparatuses 10 may not indicate the patient suite 42 in which the corresponding support apparatuses 10 is located. Accordingly, in response to an authenticated connection to one of the support apparatuses 10, for example, the second support apparatus 10b located in the second patient suite 42b, the controller 20 of the second support apparatus 10b may control the indicator device 34 to activate the second indicator 34b. In this way, the controller 20 may activate the second indicator 34b to illuminate, such that the user 62 may identify that the second support apparatus 10b is the device connected to the service unit 32. Accordingly, based on this information, the user 62 may proceed with a service update or maintenance operation for the second support apparatus 10b confidently knowing that the second patient support apparatus 10b is the connected device rather than one of the remaining support apparatuses 10 within the detection range 70.

Once communication is established between the service unit 32 and the support apparatus 10 (e.g., the second support apparatus 10b), the controller 20 may activate the third indicator 34c to identify a confirmation of one or more operations controlled or communicated to the controller 20. For example, in response to a completion of an activity or process of the support apparatus 10, the controller 20 may activate the third indicator 34c to output a visual indication that the activity is complete. For example, the controller 20 may activate the third indicator 34c in response to the completion of an activated feature, a control instruction, a configuration application, a software or firmware update, or various other processes. Such activity may be controlled by the controller 20 in response to a communication from the service unit 32 communicated via the communication interface 30. Accordingly, the indication device 34 may be configured to output visual indications identifying a variety of activities related to the operation of the support apparatus 10 including the operation of various devices and/or peripherals (e.g., remote devices 60) in communication with the support apparatus 10.

Referring now to FIGS. 3, 4, 5, and 6, graphical representations of an application interface 80 of the service unit 32 are described in reference to the operation of the support apparatus 10. As previously discussed, the application interface 80 may display an address list 82 identifying the address (e.g., IP address) of each of the controllers 20 and corresponding support apparatuses 10 within the detection range 70. The support apparatuses 10, or more generally the remote devices 60, identified within the detection range 70 may correspond remote devices 60 with detected transmission strengths exceeding a predetermined threshold, which may correspond to a preferred detection range or a boundary at which the communication with the service unit may be viable. Accordingly, the operation of the service unit may be configured to suit a variety of operating conditions and preferences.

In addition to the address list 82, the application interface 80 may further demonstrate an inventory list 84, a service list 86, a signal strength meter 88, and a connection selection input 90. In addition to the addresses of each of the support apparatuses 10 within the detection range 70, the address list 82 may further provide a signal strength identification 92 indicting which of the support apparatuses 10 is closest in proximity based on overall signal strength. Accordingly, the addresses in the address list 82 may be organized based on the greatest signal strength and generally the corresponding closest proximity of each of the support apparatuses 10, which may aid the user 62 in distinguishing the support apparatuses 10 from one another. The application interface 80 may further include the inventory list 84, which may identify each of the patient support apparatuses 10 or, more generally, remote devices that have been reported in the inventory of the hospital building 40. While the inventory list 84 may be informative, one or more of the remote devices 60 in the inventory list 84 may not be scheduled for service by the user 62. Accordingly, the application interface 80 may further include the service list 86, which may identify a subset of the remote devices 60 or support apparatuses 10 scheduled for service during the visit by the user 62. Accordingly, the inventory list 84 and the service list 86 may be utilized by the user 62 to organize and track the support apparatuses 10 and, more generally, various types of remote devices 60 that may be controlled, updated, and/or serviced by the service unit 32.

Once one of the detected address is selected, as indicated by the connection selection input 90, the application interface 80 of the service unit 32 may display a directional signal strength indicator 94 identifying a proportional direction of the communication signal communicated from a selected address 96. The direction and strength of the signal of the selected address 96 may be identified by the service unit 32 based on an angle of arrival and an angle of departure of communication signals transmitted to and from the controller 20 of the patient support apparatus 10. In this way, the application interface 80 of the service unit 32 may provide an identification of a direction of the patient support apparatus 10 corresponding to the selected address 96, such that the user 62 may easily traverse the hallway 64 and identify the location of the patient support apparatus 10 to which the selected address 96 is assigned. As previously discussed, once the controller 20 of the patient support apparatus 10 is connected to the service unit 32, the controller 20 may activate the second indicator 34b of the indicator device 34, such that the user 62 may verify that the connected device is the device believed to be in communication with the service unit 32. In this way, the service unit 32 may guide the user 62 to the support apparatus 10 to which the selected address 96 is assigned and communicate with the controller 20 of the corresponding patient support apparatus 10 to activate the second indicator 34b, thereby verifying that the service unit 32 is in communication with the desired support apparatus 10.

As previously discussed, in the event an activity or process of the support apparatus 10 is completed, the controller 20 may activate the third indicator 34c to output a visual indication that the activity is complete. For example, once the communication between the controller 20 and the service unit 32 is established, the service unit 32 may be utilized to communicate one or more instructions or request indications of the status of the operation of the support apparatus 10 or a connected device. In response to the completion of an activated feature, a control instruction, a configuration, a software or firmware update, or various other processes; the controller 20 may activate the third indicator 34c. Similarly, the controller 20 may illuminate the third indicator 34c or a fourth indicator (not shown) to indicate that the instruction or activity was not successfully completed. In some examples, the third indicator 34c may be activated by the controller 20 to illuminate in a first color indicating a confirmation of an activity or operation of the support apparatus 10. Additionally, the controller may activate the third indicator 34c in a second color indicating a failure of an activity or operation of the support apparatus 10. Accordingly, the indication device 34 may be configured to output visual indications identifying a variety of activities related to the operation of the support apparatus 10 including the operation of various devices and/or peripherals (e.g., remote devices 60) in communication with the support apparatus 10.

Figure 4:
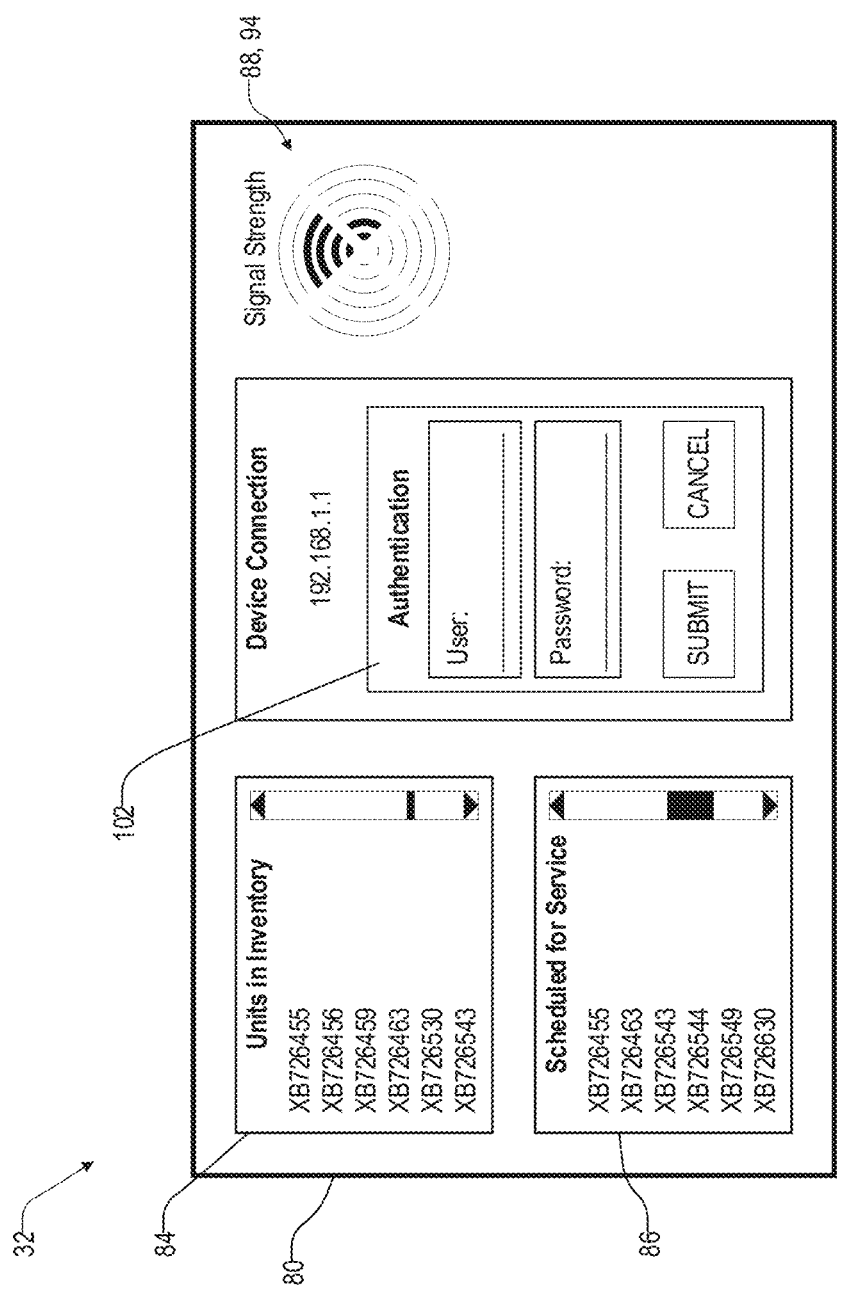
FIG. 4 is a graphical representation of an application interface of a service unit in wireless communication with a patient support apparatus.

Referring now to FIG. 4, an authentication entry 102 of the application interface 80 may be presented to authenticate a login by the user 62 to the controller 20 of the support apparatus 10 corresponding to the selected address 96, as previously discussed in reference to FIG. 3. Accordingly, the application interface 80 of the service unit 32 may display the authentication entry 102 on a display screen or interface of the service unit 32 in response to a selection of the connection selection input 90. Once prompted, the user 62 may enter authentication information or credential (e.g., a user name, password, access code, etc.), such that an authenticated connection may be established between the controller 20 of the patient support apparatus 10 and the service unit 32.

Figure 5:
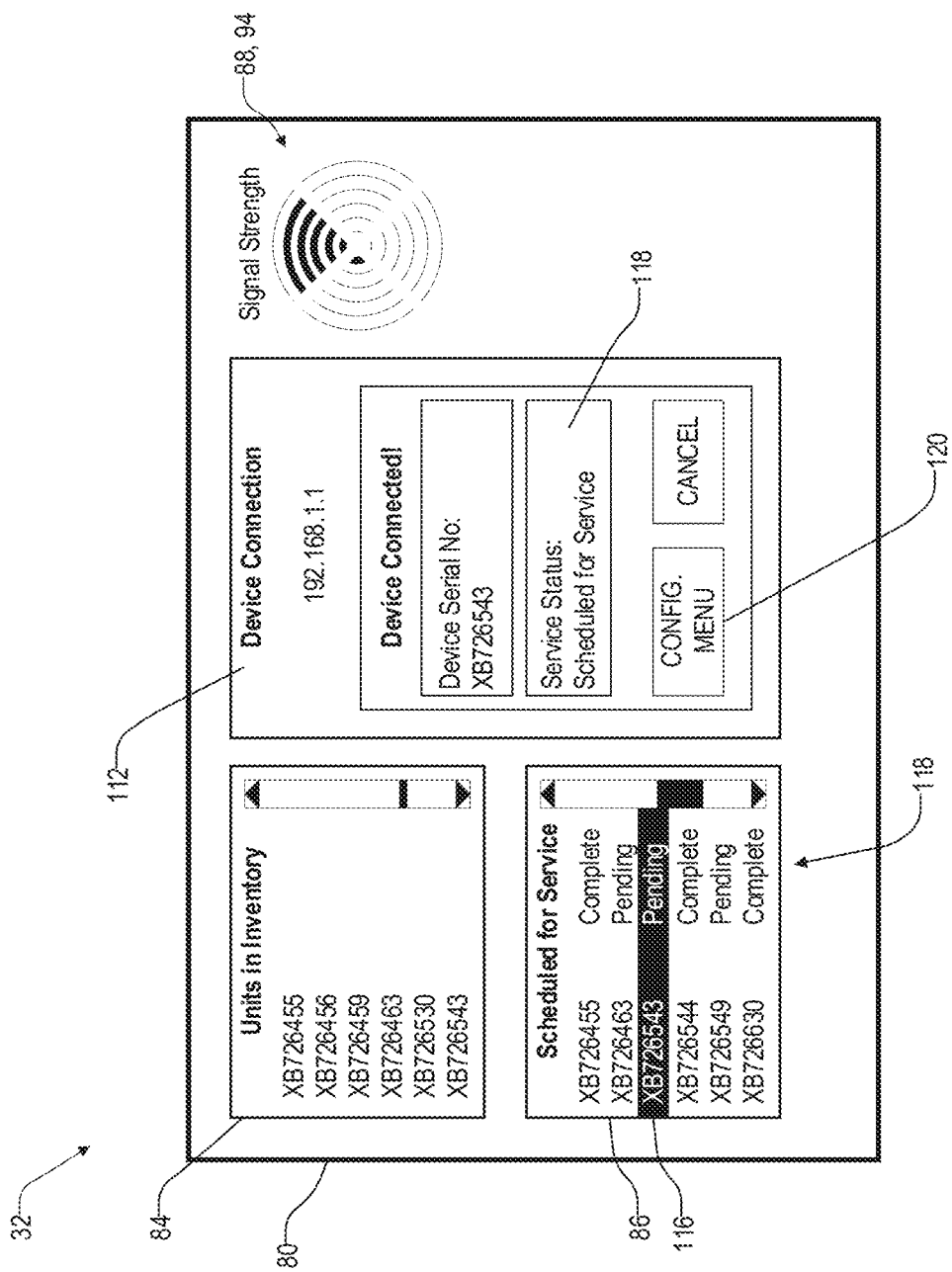
FIG. 5 is a graphical representation of an application interface of a service unit in wireless communication with a patient support apparatus.

Referring now to FIG. 5, a device connection indication 112 may be depicted on the application interface 80 in response to successful access by the authentication entry 102. Once the service unit 32 has established communication with the controller 20 of the support apparatus 10, the controller 20 may communicate a serial number. Once the serial number is received by the service unit 32, the service unit 32 may compare the serial number to the inventory list 84 and the service list 86. Based on this comparison, the service unit 32 may control the application interface 80 to indicate whether the serial number received from the controller 20 of the support apparatus 10 is identified in the service list 86. The identification of the serial number in the service list 86 is denoted as reference 116, which further demonstrates a service status indication 118. The service status indication 118 may be provided for each of the serial numbers of the remote devices 60 or support devices 10 included in the service list 86. If the serial number received from the controller 20 of the support apparatus 10 is not included in the service list 86, the service unit 32 may highlight the serial number in the inventory list 84 and may also output a notification indicating that the serial number is not included in the inventory list 84 or the service list 86. In this way, the control system 26 provides for convenient access and operation to assist in the remote access of the patient support apparatus 10 as well as various remote devices 60 compatible with the service unit 32.

Figure 6:
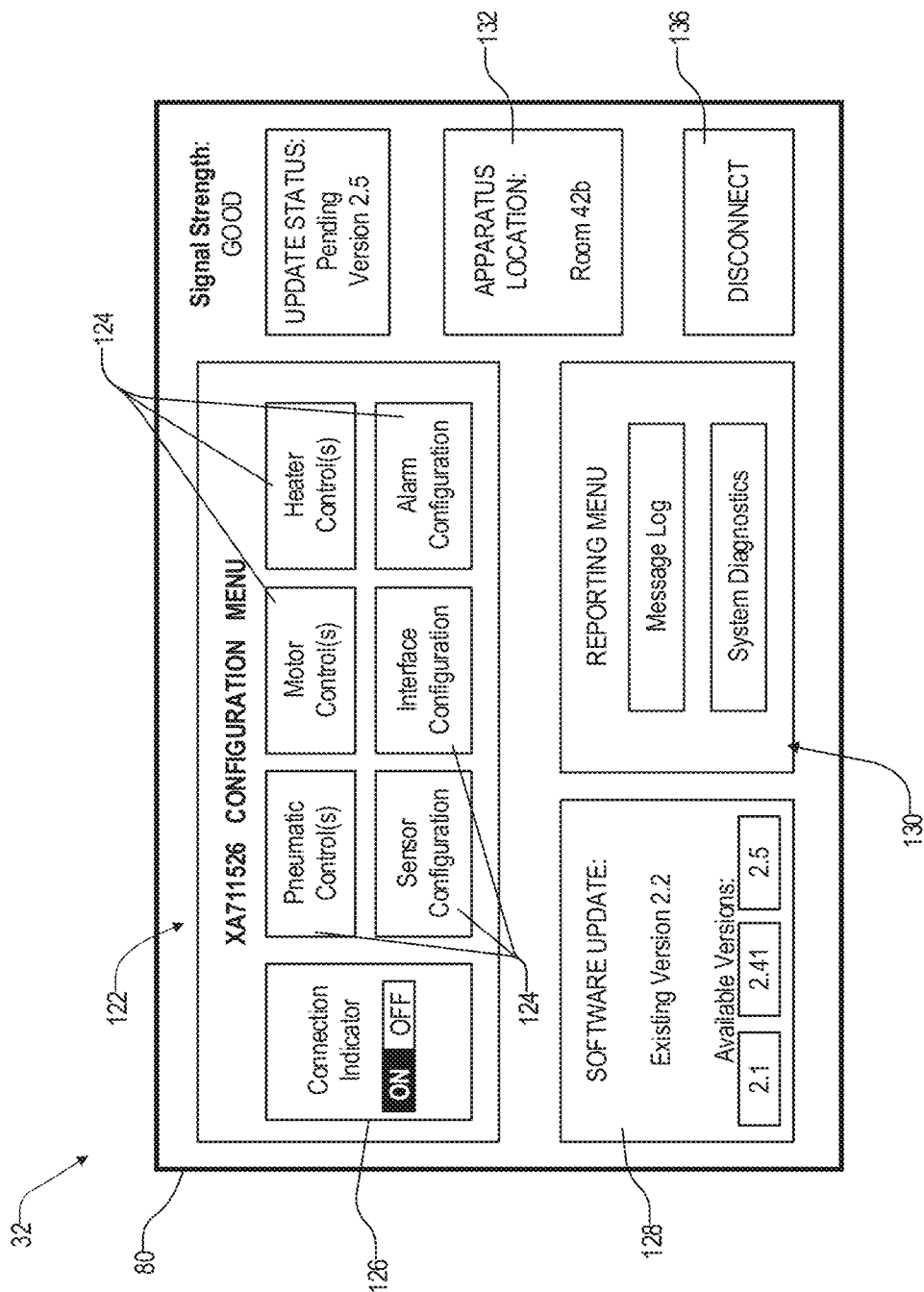
FIG. 6 is a graphical representation of an application interface of a service unit demonstrating a configuration menu of a remotely accessed device.

The connection indication 112 demonstrated in FIG. 5 may further provide for a configuration menu input 120 that may control the service unit 32 to update the application interface 80 to demonstrate a configuration menu 122 as depicted in FIG. 6. Referring now to FIG. 6, the configuration menu 122 may provide for control inputs 124 configured to control each of the sensors 22, the control devices 24, an interface configuration, and an alarm configuration of the patient support apparatus 10. The control inputs 124 may also provide for an indicator control input 126 that may be configured to instruct the controller 20 to selectively activate or deactivate the indicators 34a, 34b, 34c of the indicator device 34. Accordingly, the configuration menu 122 of the service unit 32 may provide for remote control and/or programming of various systems or connected accessories of the support apparatus 10.

The configuration menu 122 may further provide for a selection of a software version via a software update input 128 as well as a reporting menu 130 including a message log and system diagnostic menu of the controller 20. A location input 132 may be configured to receive and store a location of the patient support apparatus 10 as identified by the user 62 during the service visit. For example, referring again to the example of FIG. 2, the user 62 may enter the location of the support apparatus 10 as the second patient suite 42b in the location input 132 at the time of service. Accordingly, the location of the support apparatus 10 can be documented by the system 26. Finally, the configuration menu 122 may include a disconnect input 136 that may terminate the authenticated wireless communication between the controller 20 of the support apparatus 10 (i.e., the second support apparatus 10b based on the example of FIG. 2 in the second patient suite 42b and the service unit 32). Once disconnected, the controller 20 of the support apparatus 10 may deactivate the second indicator 34b.

Figure 7:
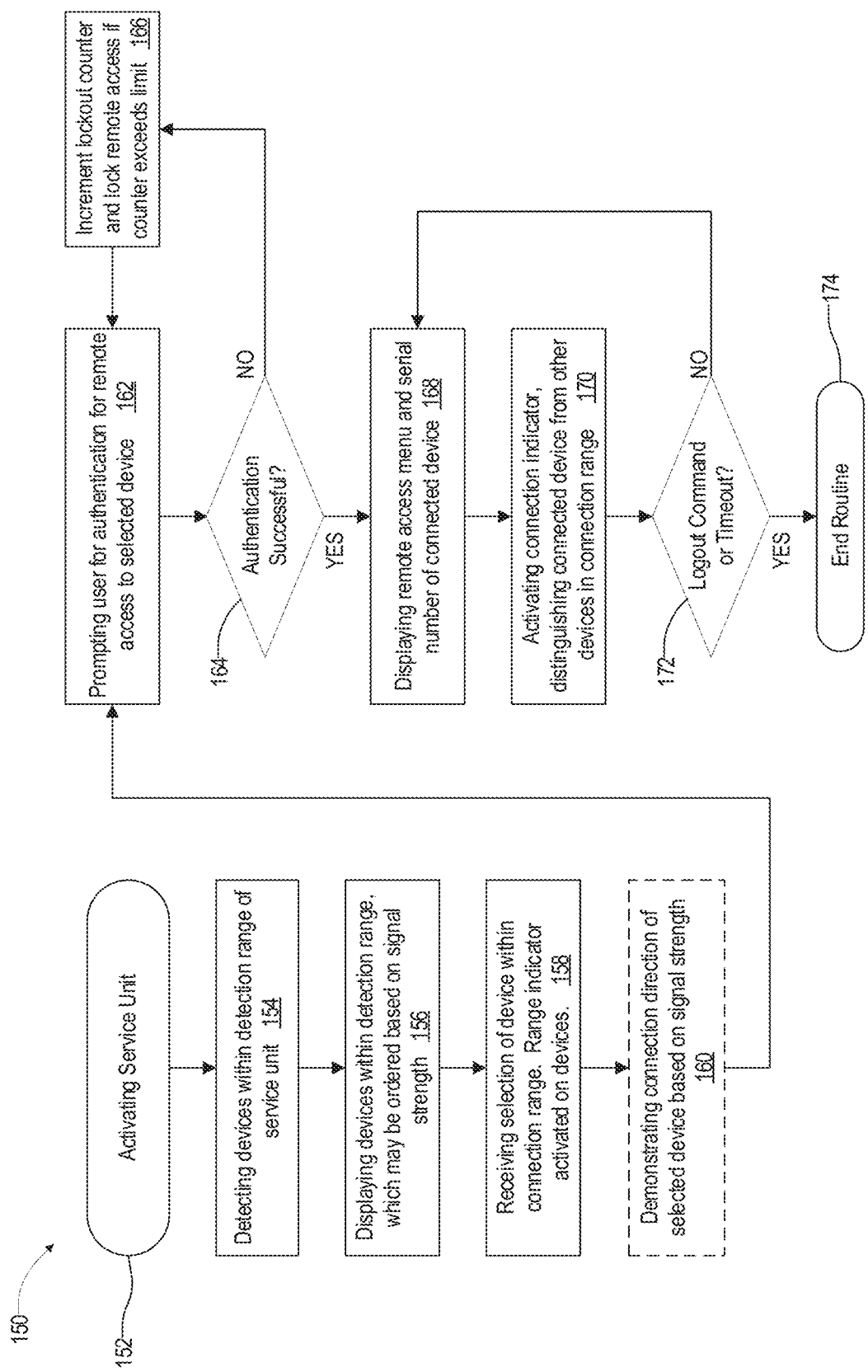
FIG. 7 is a flow chart of a method of processing a service operation for a patient support apparatus via a remote access procedure.

Referring now to FIG. 7, a flow chart of a method 150 of establishing wireless communication between the service unit 32 and the patient support apparatus 10 is shown. The method 150 is discussed generically in reference to the remote devices 60 rather than the patient support apparatuses 10 for clarity. The method may begin in step 152 in response to the activation of the service unit 32. Once activated, the service unit 32 may monitor wireless transmission signals via the communication circuit and detect the remote devices 60 within the detection range 70 of the wireless communication interface 30 (154). Once the remote devices 60 are identified, the service unit 32 may continue by displaying the addresses of the remote devices 60 within the detection range 70 on the application interface 80 (156). As previously discussed, the remote devices 60 within the detection range 70 may be organized in the address list 82 based on a relative signal strength of the wireless communication via the wireless communication interface 30.

Upon receiving a selection of the selected address 96 of one of the remote devices 60, for example the second support apparatus 10b as depicted in FIG. 2, the service unit 32 may activate the signal strength meter 88 to indicate the relative signal strength of the remote device 60 to which the selected address 96 is assigned (158). Additionally, in an exemplary embodiment, the service unit 32 may be operable to display a directional signal strength of the remote device 60 for the selected address 96 based on an angle of arrival or angle of departure directional signal determination, which may be supported by some wireless protocols (e.g., Bluetooth® Low Energy (BLE), Ultra-Wideband, etc.) (160). Following step 160, the method 150 may continue by prompting the user 62 for authentication by displaying the authentication entry 102 on the application interface 80 (162).

In step 164, the service unit 32 may identify whether or not the authentication from step 162 is successful. If the authentication is not successful, the method 150 may continue by incrementing a lockout counter and potentially locking remote access to the controller 20 of the remote device 60 if the counter exceeds a counter limit for multiple unsuccessful authentication attempts (166). If the authentication in step 164 is successful, the method 150 may continue by displaying the configuration menu 122, which may include an identification of a serial number of the remote device 60 in communication with the service unit 32 (168). Additionally, once the communication is established, the controller 20 of the remote device 60 (e.g., the patient support apparatus 10) may control the indicator device 34 to activate the second indicator 34b (170). In this way, the controller 20 of the remote device 60 may control the indicator device 34 to visually distinguish the remote device 60 connected to the service unit 32 from the remaining remote devices 60 that may be within the detection range 70. The method 150 may continue to step 172 where the service unit 32 monitors for the disconnect input 136 or an inactivity timeout. Upon receipt of the disconnect input 136 or as a result of the inactivity timeout on the service unit 32, the method 150 may continue to step 174 and end the remote access routine disconnecting the connection between the service unit 32 and the remote device 60.

Referring to FIG. 8, a block diagram of the control system 26 is shown demonstrating the support apparatus 10 in communication with the hospital network 28 and a plurality of the remote devices 60 via the wireless interface 30. The hospital network 28 may include a combination of wired connections (e.g., Ethernet) as well as wireless networks, which may include the wireless interface 30. Accordingly, the support apparatus is shown incorporated as a node of a wireless interface 30 in communication with the hospital network 28. As shown, wireless interface 30 may include a variety of electronic devices, which may be configured to communicate over various wired or wireless communication protocols. Accordingly, the support apparatus 10 is accompanied by additional remotely accessible devices 60, which may correspond to additional patient support apparatuses 10 or may correspond to a variety of devices in communication with the wireless interface 30. In this configuration, the service unit 32 may be in wireless communication with each of the remotely accessible devices 60 and provide for remote access and control of the support apparatuses 10.

The wireless interface 30 may be implemented as a mesh or internet of things (IoT) network, wherein each of a plurality of connected devices (e.g., the support apparatus 10, the remote devices 60, the service unit 32, etc.) is operable to communicate directly with one another via the wireless interface 30. Additionally, the wireless interface 30 may be in communication with a wireless router 178 through which the remotely accessed devices 60 may be in communication with one another as well as a local hospital server or remote server 180 via the hospital network 28. Accordingly, the wireless interface 30 permits coordinated control and programming of each of the connected remote devices 60 via a hierarchical control structure and/or via a distributed communication structure.

The support apparatus 10 may provide for programmable operation via the controller 20. As disclosed, the controller 20 is configured to control various components and/or integrated circuits to provide for the control of the control devices 24 in response to the sensors 22 as well as controls communicated via the application interface 80 of the service unit 32. The controller 20 may include various types of control circuitry, digital and/or analog, and may include a processor 182, microcontroller, application-specific integrated circuit (ASIC), or other circuitry configured to perform various input/output, control, analysis, and other functions as described herein. The controller 20 further includes a memory 184 configured to store one or more control routines 186, which may include operating instructions to enable the methods discussed herein. The memory 184 may be implemented by a variety of volatile and non-volatile memory formats. One or more communication circuits 188 of the support apparatus 10 may be incorporated with the controller 20 or in communication with the controller 20 to permit communication via the wireless interface 30 or various protocols of wireless communication in combination with wired network communication.

In operation, the controller 20 of the control system 26 receives power from a power supply 190, which may further be configured to supply power to the sensors 22, the control devices 24, and various components of the support apparatus 10. The power supply 190 may include one or more transformers, rectifiers, capacitors, and various electrical components to condition the power for the operation of the support apparatus 10. The actuator system 24a may comprise a plurality of motors and mechanical actuators configured to adjust the support apparatus 10 into various positions in response to inputs to the user interface 16. For example, the actuator system 24a may control raising and lowering portions of the frame 12 and control movements of various support sections or deck sections of the mattress 14, such as head, thigh, and foot sections, relative to portions of the frame 12. The pneumatic system 24b operates to inflate and deflate portions of a mattress 14 of the support apparatus 10. For example, the user inputs 16a may instruct the controller 20 to control a mattress therapy function of the mattress 14 of the support apparatus 10. The heating apparatus 24c may include one or more heating elements incorporated in portions of the mattress 14 and may also be controlled based on inputs received by the controller 20 via the user interface 16.

In addition to the control devices 24, the support apparatus 10 may further comprise one or more of the sensors 22.

The sensors 22 may include angle sensors temperature sensors, pressure sensors, weight sensors, etc. configured to monitor the operations of the support apparatus 10 and the status of a patient occupying the apparatus 10. The controller 20 may further be in communication with an alarm 16c or speaker of the user interface 16 configured output audible alerts or notifications related to the operation of the support apparatus 10 and/or additional devices or accessories of the system 26. In this way, the controller 20 may operate to detect, control, and communicate the status of the support apparatus 10 and/or the system 26.

In addition to the sensors 22 and the control devices 24, the support apparatus 10 may further comprise one or more accessory module(s) 192 that may be controlled by or in communication with the controller 20 via the wireless communication interface 30 or a wired connection. For example, the accessory module(s) 192 may correspond to one or more remote sensors, actuators, user interfaces, etc. in communication with the controller 20 via the communication circuit 188. In this configuration, the controller 20 may be configured to receive sensor information from various devices and/or peripherals, which may be distributed in a patient suite 42 and/or throughout the building 40. The accessory module(s) 192 may include one or more valves, sensors, actuators, remote controls, and a variety of other accessories that may be implemented in the operating environment of the support apparatus 10. Accordingly, the disclosure provides for a scalable and flexible system that may be utilized to monitor and control a variety of remote devices 60.

Still referring to FIG. 8, the wireless interface 30 may be implemented via one or more direct or indirect, non-hierarchical communication protocols, including but not limited to Bluetooth®, Bluetooth® Low Energy (BLE), Thread, Ultra-Wideband, Z-Wave, ZigBee, etc. In this configuration, the remote devices 60 (e.g., the support apparatuses 10) may operate via a decentralized control structure. Additionally, the wireless interface 30 may correspond to a centralized or hierarchical communication interface wherein one or more of the remote devices 60 communicate via the router 178 (e.g., a communication routing controller). Accordingly, the wireless interface 30 may be implemented via a variety of communication protocols in various combinations, including but not limited to, global system for mobile communication (GSM), general packet radio services (GPRS), code division multiple access (CDMA), enhanced data GSM environment (EDGE), fourth-generation (4G) wireless, fifth-generation (5G) wireless, Wi-Fi, world interoperability for microwave access (WiMAX), local area network (LAN), Ethernet, etc. By flexibly implementing the wireless communication interface 30, the support apparatus 10 may be in communication with one or more of the remote devices 60 and the remote server 180 directly, via the router 178 and/or via a cellular data connection.

The service unit 32 may correspond to an electronic communication device (e.g., cell phone, tablet, smartphone, etc.). In some embodiments, electronic communication devices may include other electronic devices, such as laptops, personal computers, and/or other devices. The service unit 32 may be configured to run various software applications and present the application interface 80 to report and receive inputs to adjust the settings of the controller 20 of the support apparatus 10 as well as the remote devices 60 in connection with the wireless interface 30. The software operating on the service unit 32 may enable the control of multiple remotely accessible devices 60 and/or discrete systems, which may be separately monitored and documented in separate databases or servers of the hospital network 28. Accordingly, the service unit may be configured to communicate with a variety of implementations of the remote devices 60.

The system disclosed herein is further summarized in the following paragraphs and is further characterized by combinations of any and all of the various aspects described therein.

According to one aspect of the present disclosure, a patient support apparatus, including a connection indicator, is disclosed. The apparatus comprises a visual indicator in connection with a portion of the patient support apparatus. The visual indicator is configured to output a first indication and a second indication. The support apparatus comprises a communication circuit configured to communicate via a wireless communication interface and a controller configured to communicate with a service unit via the wireless communication interface. The controller is configured to activate the first indication in response to the service unit detected within a detection range, and, in response to enabling a remote access to the service unit, the controller is configured to activate the second indicator. The activation of the second indicator identifies the controller of the patient support apparatus is in communication with the service unit via the wireless communication interface.

In various aspects, the disclosure may further provide for one or more of the following features:
- the controller is further configured to receive a communication from the service unit identifying a request for remote access of the controller;
- the visual indicator comprises an indication device comprising at least one light emitter configured to output the first indication as a first light emission and the second indication as a second light emission;
- the visual indicator comprises a light projector configured to project the first indication and the second indication on a surface proximate the patient support apparatus;
- the visual indicator comprises a directional adjustment apparatus configured to adjust a projection direction of at least one of the first indication and the second indication;
- the patient support apparatus is one of a plurality of patient support apparatuses in a facility and each of the plurality of the patient support apparatuses comprises the indicator device configured to output the first indication and the second indication;
- each of the controllers of the plurality of the patient support apparatuses activates the first indication in response to the service unit within the detection range;
- one of the controllers of the patient support apparatuses activates the second indication in response to the remote access;
- the activation of the second indication distinguishes the remote access of the one of the controllers from each of the remaining controllers of the patient support apparatuses within the detection range; and/or
- the controllers of the patient support apparatuses within the detection range without the remote access enabled do not activate the second indication.

According to another aspect of the disclosure, a method for operating a patient support apparatus is disclosed. The method comprises monitoring a wireless communication interface for a service unit and detecting the service unit within a detection range. In response to detecting the service unit within the detection range, a first indication of a visual indicator is activated. The method further comprises receiving an authentication from the remote service unit and enabling a remote access to a controller of the patient support apparatus in response to the authentication. In response to enabling the remote access to the controller, a second indication of the visual indicator is activated. The second indication identifies the controller in communication with the service unit via the wireless communication interface.

In various aspects, the disclosure may further provide for one or more of the following features:
- the patient support apparatus is one of a plurality of patient support apparatuses in a facility and each of the plurality of the patient support apparatuses comprises the indicator device configured to output the first indication and the second indication;
- each of the controllers of the plurality of the patient support apparatuses activates the first indication in response to detecting the service unit within the detection range; and/or
- distinguishing a first support apparatus of the plurality of patient support apparatuses from a remaining group of the plurality of patient support apparatuses by activating the second indication on the first support apparatus in response to the enabling of the remote access.

According to yet another aspect of the disclosure, a patient support apparatus includes a visual indicator in connection with a portion of the patient support apparatus. The visual indicator is configured to output a first indication and a second indication from the portion of the patient support apparatus. A communication circuit is configured to communicate via a wireless communication interface. A controller is configured to communicate with a service unit via the wireless communication interface. In operation, the controller activates the first indication in response to the service unit detected within a detection range of the wireless communication interface. The controller may further receive a control instruction from the service unit via the wireless communication interface. In response to processing the control instruction, the controller activates the second indicator identifying a confirmation of a completion of the control instruction.

In various aspects, the disclosure may further provide for one or more of the following features:
- the control instruction comprises at least one of a feature activation, a configuration update, and a software or firmware update;
- the control instruction is a request for a remote access of the controller from the service unit;
- the activation of the second indicator is in response to enabling the remote access of the service unit;
- the second indicator identifies the controller of the patient support apparatus in communication with the service unit via the wireless communication interface;
- the control instruction comprises authentication information authenticating the request for the remote access;
- the controller is further configured to enable the remote access of the controller by the service unit in response to the authentication information corresponding to authorized credentials;
- an actuator configured to control a position of a mattress; and/or
- the control instruction comprise a control command that instructs the controller to control the actuator to adjust the position of the mattress.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent or may be removable or releasable unless otherwise stated.

The various illustrative logical blocks, modules, controllers, and circuits described in connection with the embodiments disclosed herein may be implemented or performed with application-specific integrated circuits (ASICs), field-programmable gate arrays (FPGAs), general-purpose processors, digital signal processors (DSPs) or other logic devices, discrete gates or transistor logic, discrete hardware components, or any combination thereof designed to perform the functions described herein. A general-purpose processor may be any conventional processor, controller, microcontroller, state machine, or the like. A processor may also be implemented as a combination of computing devices, e.g., a combination of a DSP and a microprocessor, a plurality of microprocessors, one or more microprocessors in conjunction with a DSP core, or any other such configuration.

It is also important to note that the construction and arrangement of the elements of the disclosure, as shown in the exemplary embodiments, are illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, elements shown as multiple parts may be integrally formed, the operation of the interfaces may be reversed or otherwise varied, the length or width of the structures and/or members or connector or other elements of the system may be varied, and the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A patient support apparatus comprising:
   a visual indicator in connection with a portion of the patient support apparatus, the visual indicator configured to output a first indication and a second indication;
   a communication circuit configured to communicate via a wireless communication interface; and
   a controller configured to communicate with a service unit via the wireless communication interface, the controller configured to:
   activate the first indication in response to the service unit detected within a detection range; and
   in response to enabling a remote access to the service unit, activate the second indicator identifying the controller of the patient support apparatus in communication with the service unit via the wireless communication interface, wherein the activation of the second indication distinguishes the remote access of the controller from other controllers within the detection range.

2. The patient support apparatus according to claim 1, wherein the controller is further configured to:
   receive a communication from the service unit identifying a request for remote access of the controller.

3. The patient support apparatus according to claim 1, wherein the visual indicator comprises an indication device comprising at least one light emitter configured to output the first indication as a first light emission and the second indication as a second light emission.

4. The patient support apparatus according to claim 1, wherein the visual indicator comprises a light projector configured to project the first indication and the second indication on a surface proximate the patient support apparatus.

5. The patient support apparatus according to claim 1, wherein the visual indicator comprises a directional adjustment apparatus configured to adjust a projection direction of at least one of the first indication and the second indication.

6. The patient support apparatus according to claim 1, wherein the patient support apparatus is one of a plurality of patient support apparatuses in a facility and each of the plurality of the patient support apparatuses comprises the indicator device configured to output the first indication and the second indication.

7. The patient support apparatus according to claim 6, wherein each of the controllers of the plurality of the patient support apparatuses activates the first indication in response to the service unit within the detection range.

8. The patient support apparatus according to claim 6, wherein the one of the controllers of the patient support apparatuses activates the second indication in response to the remote access.

9. The patient support apparatus according to claim 8, wherein the activation of the second indication distinguishes the remote access of the one of the controllers from the other controllers of the patient support apparatuses within the detection range.

10. The patient support apparatus according to claim 8, wherein the other controllers of the patient support apparatuses within the detection range without the remote access enabled do not activate the second indication.

11. A method for operating a first patient support apparatus in a facility among a plurality of patient support apparatuses, the method comprising:
   monitoring a wireless communication interface for a service unit;
   detecting the service unit within a detection range;

activating a first indication of a visual indicator in response to detecting the service unit within the detection range;

receiving an authentication from a remote service unit;

enabling a remote access to a controller of the first patient support apparatus in response to the authentication;

in response to enabling the remote access to the controller, activating a second indication of the of the visual indicator, wherein the second indication identifies the controller in communication with the service unit via the wireless communication interface; and distinguishing the first patient support apparatus of the plurality of patient support apparatuses from a remaining group of the plurality of patient support apparatuses within the detection range by activating the second indication on the first support apparatus in response to the enabling of the remote access.

12. The method according to claim 11, each of the plurality of the patient support apparatuses comprises the indicator device configured to output the first indication and the second indication, and wherein each of the controllers of the plurality of the patient support apparatuses activates the first indication in response to detecting the service unit within the detection range.

13. A patient support apparatus comprising:

a visual indicator in connection with a portion of the patient support apparatus, the visual indicator configured to output a first indication and a second indication from the portion of the patient support apparatus;

a communication circuit configured to communicate via a wireless communication interface; and a controller configured to communicate with a service unit via the wireless communication interface, the controller configured to:

activate the first indication in response to the service unit detected within a detection range of the wireless communication interface;

receive a control instruction from the service unit via the wireless communication interface; and in response to processing the control instruction, activate the second indicator identifying a confirmation of a completion of the control instruction, wherein the activation of the second indicator distinguishes the controller from other controllers within the detection range.

14. The patient support apparatus according to claim 13, wherein the control instruction comprises at least one of a feature activation, a configuration update, and a software or firmware update.

15. The patient support apparatus according to claim 13, wherein the control instruction is a request for a remote access of the controller from the service unit.

16. The patient support apparatus according to claim 13, wherein the activation of the second indicator is in response to enabling the remote access of the service unit.

17. The patient support apparatus according to claim 13, wherein the second indicator identifies the controller of the patient support apparatus in communication with the service unit via the wireless communication interface.

18. The patient support apparatus according to claim 13, wherein the control instruction comprises authentication information authenticating the request for the remote access.

19. The patient support apparatus according to claim 18, wherein the controller is further configured to:

enable the remote access of the controller by the service unit in response to the authentication information corresponding to authorized credentials.

20. The patient support apparatus according to claim 13, further comprising:

an actuator configured to control a position of a mattress.

21. The patient support apparatus according to claim 20, wherein the control instruction comprises a control command that instructs the controller to control the actuator to adjust the position of the mattress.

22. The patient support apparatus according to claim 1, wherein the remote access comprises the access of a status or a communication of a control instruction to the controller of the patient support apparatus.

* * * * *